United States Patent
Grundei

[11] Patent Number: 6,149,689
[45] Date of Patent: Nov. 21, 2000

[54] IMPLANT AS BONE REPLACEMENT

[75] Inventor: Hans Grundei, Lübeck, Germany

[73] Assignee: Eska Implants GmbH & Co., Lubeck, Germany

[21] Appl. No.: 09/083,288

[22] Filed: May 22, 1998

Related U.S. Application Data

[63] Continuation of application No. PCT/EP96/05018, Nov. 15, 1996.

[30] Foreign Application Priority Data

Nov. 22, 1995 [DE] Germany .................. 195 43 530

[51] Int. Cl.[7] ........................................................ A61F 2/36
[52] U.S. Cl. ........................................ 623/23.5; 623/23.54
[58] Field of Search .................... 623/22, 23, 16; 164/34, 35; 75/255; 428/553

[56] References Cited

U.S. PATENT DOCUMENTS

| | | | |
|---|---|---|---|
| 3,424,227 | 1/1969 | Watts et al. | 428/553 |
| 4,365,358 | 12/1982 | Judet et al. | 3/1.912 |
| 4,550,448 | 11/1985 | Kenna . | |
| 4,673,409 | 6/1987 | Van Kampen | 623/23 |
| 4,828,563 | 5/1989 | Muller-Lierheim | 623/16 |
| 5,178,201 | 1/1993 | Ahlers | 164/34 |
| 5,433,750 | 7/1995 | Gradinger et al. | 623/16 |

FOREIGN PATENT DOCUMENTS

| | | |
|---|---|---|
| 0 159 036 A2 | 10/1985 | European Pat. Off. . |
| 0 399 163 A1 | 11/1990 | European Pat. Off. . |
| 2 356 465 | 1/1978 | France . |
| 41 06 971 C1 | 3/1992 | Germany . |
| 42 08 247 C1 | 10/1993 | Germany . |
| 43 36 551 C1 | 3/1995 | Germany . |

*Primary Examiner*—Vincent Millin
*Assistant Examiner*—Alvin Stewart
*Attorney, Agent, or Firm*—Akin, Gump, Strauss, Hauer & Feld, L.L.P.

[57] ABSTRACT

An implant is provided as a bone replacement having an open-meshed, three-dimensional structure which at least partially covers its surface and which is constructed from particles which are connected to a base structure (1) of the implant. The particles have four to eight studs (3) extending radially outward from each other, at least three of which are connected directly to the base structure. At least the ends (7) of the studs (3) projecting out freely from the base structure (1) form undercuts (8) and have a surface which is outwardly rounded off.

8 Claims, 1 Drawing Sheet

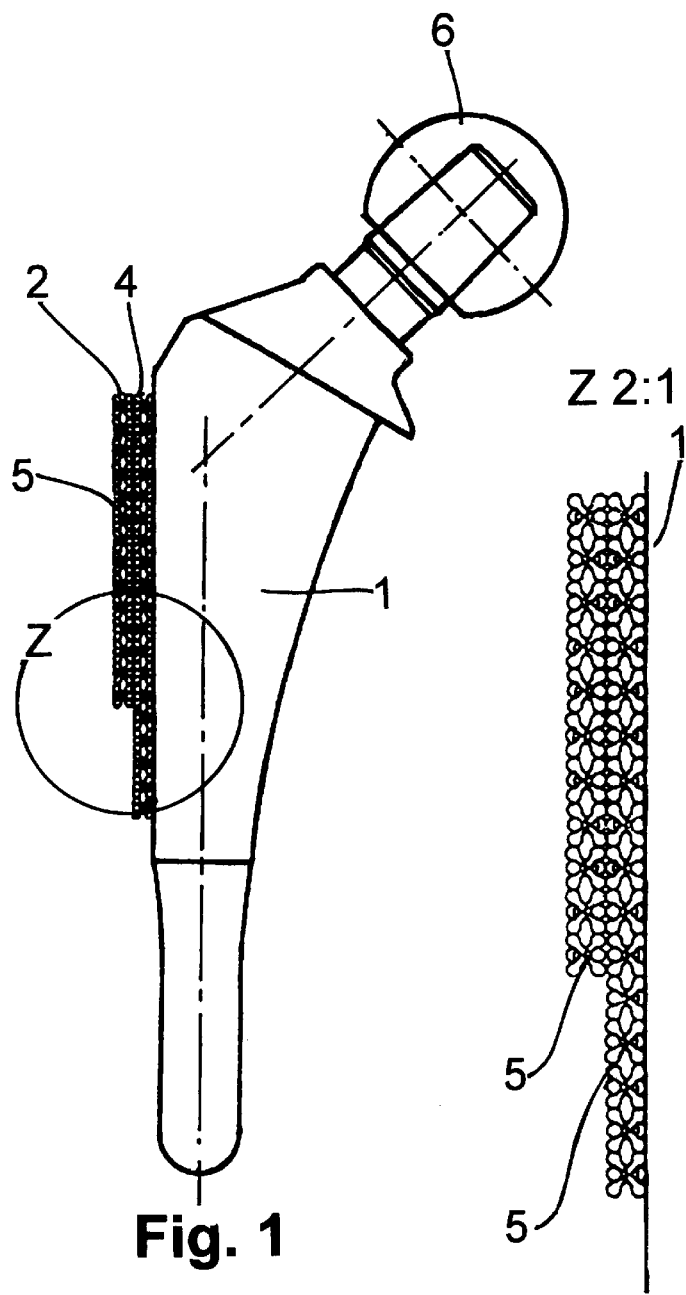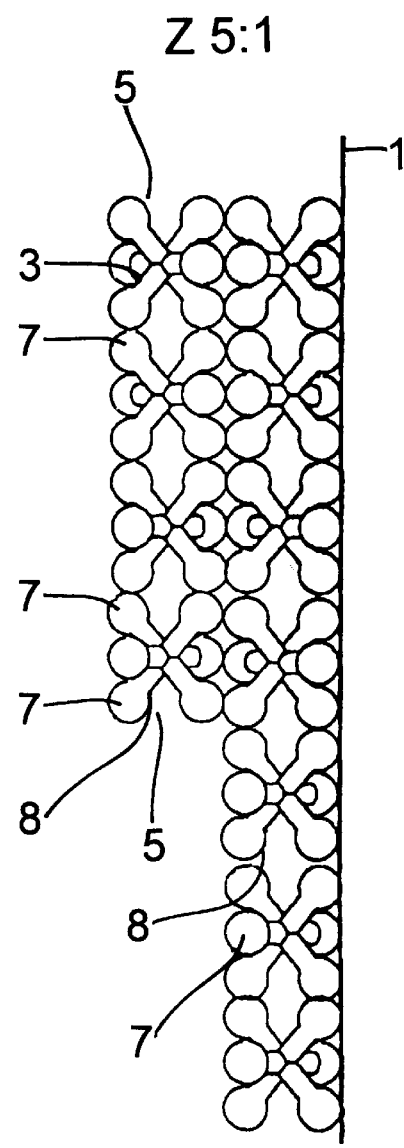
Fig. 1
Fig. 2
Fig. 3

IMPLANT AS BONE REPLACEMENT

CROSS REFERENCE TO RELATED APPLICATION

This application is a continuation of International Application PCT/EP96/05018, filed Nov. 15, 1996.

BACKGROUND OF THE INVENTION

The invention involves an implant as a bone replacement (endoprosthesis), having a base structure with a surface at least partially covered by an open-meshed, three-dimensional structure constructed from particles having four to eight studs extending radially outward from each other, at least three of the studs being directly connected to the base structure.

Such an implant is obtained, for example, by the performing the process according to German patent DE-C 41 06 971 (U.S. Pat. No. 5,178,201). An implant of this type has proven itself in recent years to be excellent, especially in regard to the planned growth into and through the three-dimensional, open-meshed structure, which at least partially covers the surface of the implant.

The growth penetration behavior of the implant can be further improved in that, according to German patent DE-C 42 08 247 (U.S. Pat. No. 5,433,750), several discrete zones having different mesh widths are generated on the surface of the implant. In the process, the mesh widths are adapted to the cellular nature and porosity of the bone material which is in contact with the surface structure of the implant after its implantation. This adaptation is in the sense that the respective mesh widths of the zones correspond approximately to the sizes of the cells and pores of the natural spongiosa, which should grow into and onto, or penetrate through, the surface structure of the implant.

As mentioned, known implants have proven themselves excellently in practice. They have a property though, which becomes noticeable in a negative way during a revision operation, i.e. when removing the implant which has grown affixed to the surrounding spongiosa material. Thus, the surface structures of the known implants are, in particular, constructed in such a jagged manner that a removal of the bone trabecula which has grown into the material is not readily possible using a suitable tool, since the tool frequently hooks onto the deeply-indented surface. This disrupts the progress of the revision operation in an undesirable way.

SUMMARY OF THE INVENTION

In view of this background, an object of the present invention is to further construct an implant of the generic type set forth at the outset in such a way that a revision operation is made easier and, compared to the known implant, an even stronger anchoring of the implant in the bone material is obtained. This object is achieved in the implant of the generic type by providing the ends of at least those studs which project freely outward from the base structure (i.e., at least those which are not directly connected to the base structure) with undercuts and an outer surface which is rounded off. Advantageous further embodiments are set forth below and in the dependent claim.

The invention thus proposes constructing the particles, which are already present in the implant of the generic type and form the open-meshed, three-dimensional structure, in a different way than the ones given, for example, in German patent DE-C-41 06 971. Thus, it is proposed that the ends of at least the studs projecting out freely from the base structure form undercuts and have a surface which is outwardly rounded. The base structure of the implant can, for example, be the massive core on which the open-meshed three-dimensional structure is to be built. Thus, at least one stud extends out from this base structure and has the specially constructed end. The ends of the stud(s) are material agglomerations rounded off to the outside, which facilitate the severing of the bone trabecula in case of a revision operation, such that in spite of the properties of the surface structure of the implant being grown into and penetrated, a tool can be conducted relatively easily over the surface of the implant, without hooking into the surface structure.

The formation of the undercuts by the rounded off material agglomerations is, however, also to be provided in view of the second part of the object upon which the invention is based. Through the undercuts, in particular, the secondary fixation of the implant can be further increased, relative to the implant of the generic type, in that the very bone trabecula which grow through the open-meshed and three-dimensional surface structure also contribute, additionally and in a purely mechanical way, to the fixation, so that in practice, the bone material grows behind the undercut via a sort of locking joint and thus contributes to an even higher fixation security.

The implant according to the present invention can, moreover, also not be manufactured by the process, as known from French published patent application FR-A-2 356 465. In that document, an investment casting process for the manufacture of surgical prostheses is described, in which the finished cast piece has an essentially granular surface, which is made up of a plurality of spheres so that slight undercuts are constructed for the bone material which is growing on the surface of the implant. The fixation security, relative to an implant of the generic type, is extremely low.

According to a preferred embodiment of the present invention, it is provided that the ends of the studs are constructed to be thickened into a crown. The crown formation can preferably be constructed ball-shaped or olive-shaped. The crowned enlargements form undercuts in these cases, which provide for a mechanical retention of the implant via the bone material which has already grown into the surface structure. On the other hand, the crowned enlargements cause defined surface inconsistencies, which do not impede a tool when severing the bone trabecula during a revision operation.

An alternative embodiment to the crowned enlargement of the ends of the studs is given by the embodiment in which the free ends of the studs are constructed in a mushroom shape with the dome arched away from the base structure of the implant (i.e., away from the center of the particle). Also, in this way, a defined inconsistency of the surface structure can be obtained, with regard to an easy revision operation. However, the surface should not be completely smooth in practice, of course, since the surrounding bone is also stimulated by the inconsistencies to grow into the surface structure.

Independently of the concrete embodiment of the ends of the particulate studs, the particles and the base structure of the implant can preferably comprise a single piece made of the same material. The material can be plastic acceptable to the body, but could also be a metal acceptable to the body. The implant is then advantageously manufactured in an investment casting (lost wax) process.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings:

FIG. 1 is a schematic view of an implant in the form of a hip joint stem;

FIG. 2 is an enlargement of the detail Z in FIG. 1 in two-fold enlargement; and

FIG. 3 shows the detail Z of FIG. 1 in five-fold enlargement.

DETAILED DESCRIPTION OF THE INVENTION

As an embodiment example, an implant in the form of a hip joint stem is shown in FIG. 1, which has a base structure 1 as a massive core, as well as a ball joint head 6. A part of the surface of the base structure 1 is covered by an open-meshed, three-dimensional structure which, in the case represented, comprises two layers 2 and 4 of particles 5 coated one on top of the other. The layers 2 and 4 are penetrated by growth of bone trabecula of the spongiosa after being implanted in a tubular bone, here in a femur bone, so that an extremely close bond occurs between the implant and the spongiosa which surrounds it.

From FIG. 2 it is clear what sort of narrow meshwork is formed by the particles 5. The bone material grows through the mesh and thus provides for a stable secondary fixation.

Details of the construction of the particles 5 can be gathered from FIG. 3. They consist here of six studs 3 which extend away from each other, at least three of which are connected to the base structure 1.

The ends 7 of the studs 3 are constructed predominately with a crown enlargement, and are indeed ball-shaped. This leads, on the one hand, to the formation of undercuts 8 behind the enlargement toward the stud 3. On the other hand, at least on the outer layer of particles, a surface is hereby formed which is outwardly rounded off, which makes easier the guidance of an instrument for detaching the bone material which has grown into the layers 2 and 4. A hooking of the severing instrument is thus unlikely during the performance of a revision operation.

As mentioned above, the formation of the undercuts 8 leads to a purely mechanically acting increase in the secondary fixation of the implant into or onto the bone, in which or on which the implant has been implanted.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

I claim:

1. An implant as a bone replacement comprising a base structure (1) having an open-meshed, three-dimensional surface structure which at least partially covers the base structure, the open-meshed, three-dimensional surface structure being formed by at least one layer of particles (5) which is connected to the base structure (1), the particles (5) comprising four to eight studs (3) extending radially outwardly from each other, at least some of the particles (5) in the at least one layer having at least three of the studs (3) directly connected to the base structure (1) and at least some of the particles having studs (3) having free ends (7) projecting outwardly from the base structure (1), wherein at least the free ends (7) have enlargements which form undercuts (8), and wherein the enlargements on the free ends (7) together form an outer, bone-contacting surface of the at least one layer which is outwardly rounded off to allow a revision instrument to be guided over the outer surface without hooking into the outer surface.

2. The implant according to claim 1, wherein at least some of the studs (3) have free ends (7) projecting at an oblique angle to the base structure (1).

3. The implant according to claim 1, wherein the ends (7) are enlarged in a crown shape.

4. The implant according to claim 1, wherein the ends (7) are enlarged in a ball shape.

5. The implant according to claim 1, wherein the ends (7) are enlarged in an olive shape.

6. The implant according to claim 1, wherein the ends (7) have a mushroom shape with a dome arched toward the base structure (1).

7. The implant according to claim 1, wherein the particles (5) and the base structure (1) comprise a single piece made from a same material.

8. The implant according to claim 7, wherein the material comprises a metal acceptable by the body, and the single piece is manufactured in an investment casting process.

* * * * *